United States Patent

Jarque et al.

[11] 4,001,414
[45] Jan. 4, 1977

[54] 1,3,4-TRIMETHYL-2-(3,4,5-TRIMETHOXYBENZYL)-1,2,5,6-TETRAHYDROPYRIDINE AND ANALGESIC COMPOSITION AND METHOD USING IT

[75] Inventors: Ricardo Granados Jarque; Juan Bosch Cartes; Jorge Canals Cabiro, all of Barcelona; Cristobal Martinez Roldan; Fernando Rabadan Peinado, both of Madrid, all of Spain

[73] Assignee: Laboratorios Made, S.A., Spain

[22] Filed: Apr. 29, 1975

[21] Appl. No.: 572,863

[30] Foreign Application Priority Data

May 4, 1974  Spain .................................. 425971

[52] U.S. Cl. ........................... 424/263; 260/297 R
[51] Int. Cl.² ............... A61K 31/44; C07D 211/70
[58] Field of Search ................ 260/297 R; 424/263

[56] References Cited

UNITED STATES PATENTS 3,553,223   1/1971   Leimgruber et al. .......... 260/295 R

*Primary Examiner*—Henry R. Jiles
*Assistant Examiner*—Bernard Dentz
*Attorney, Agent, or Firm*—Marn & Jangarathis

[57] ABSTRACT

There is disclosed a process for the preparation of 1,3,4-trimethyl-2-(3,4,5-trimethoxybenzyl)-1,2,5,6-tetrahydropyridine of formula

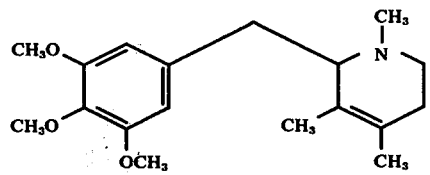

which comprises subjecting 1,3,4-trimethyl-(3,4,5-trimethoxybenzyl)-1,2,5,6-tetrahydropyridine of formula

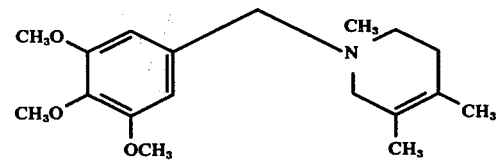

to a Stevens rearrangement in the presence of a solution of phenyl-lithium in ether under reflux of the reaction mixture, and, if desired, converting the compound of formula I produced into an addition salt thereof with a pharmaceutically acceptable acid, for example hydrochloric acid, including a pharmaceutical composition utilizing as an active ingredient 1,3,4-trimethyl-2-(3,4,5-trimethoxybenzyl)-1,2,5,6-tetrahydropyridine.

3 Claims, No Drawings

1,3,4-TRIMETHYL-2-(3,4,5-TRIMETHOXYBENZYL)-1,2,5,6-TETRAHYDROPYRIDINE AND ANALGESIC COMPOSITION AND METHOD USING IT

The present invention relates to the production of 1,3,4-trimethyl-2-(3,4,5-trimethoxybenzyl)-1,2,5,6-tetrahydropyridine

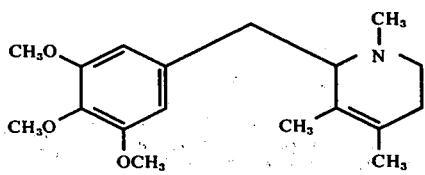

from 1,3,4-trimethyl-(3,4,5-trimethoxy-benzyl)-1,2,5,6-tetrahydropyridinium chloride (II) by a Stevens rearrangement in the presence of a solution of phenyl-lithium in ether.

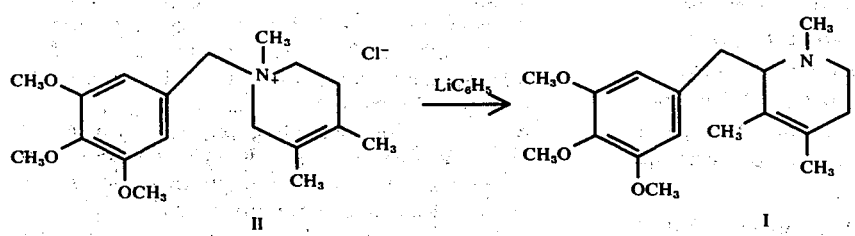

and of its addition salts with pharmaceutically acceptable acids, for example, hydrochloride (III).

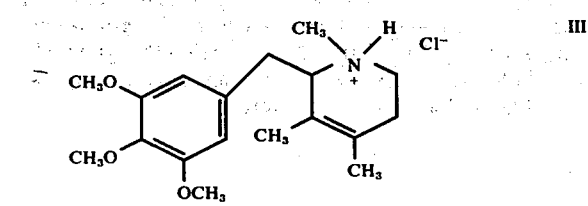

The compound mentioned is a new substance with possible pharmacological interest as an analgesic.

The process is carried out by adding the phenyl-lithium, recently prepared, to a suspension of the chloride (II) in ether, and keeping the resulting mixture under reflux. The amine fraction is extracted with dilute hydrochloric acid, is liberated with concentrated ammonium hydroxide, and is extracted with ether. Evaporation of the ether layer supplies an oil from which there is obtained by fractional distillation 1,3,4-trimethyl-2-(3,4,5-trimethoxybenzyl)-1,2,5,6-tetrahydropyridine (I) which is purified in the form of its hydrochloride.

The present invention is illustrated non-limitatively in the following example:

EXAMPLE 1

Production of 1,3,4-trimethyl-2-(3,4,5-trimethoxybenzyl)-1,2,5,6-tetrahydropyridine (I) and its hydrochloride Excess of a 1M ethereal solution of phenyl-lithium is added rapidly to a suspension of 60 g 1,3,4-trimethyl-1-(3,4,5-trimethoxybenzyl)-1,2,5,6-tetrahydropyridinium (II) chloride in ether, under a nitrogen atmosphere. The mixture is heated with reflux and with agitation for 6 hours and subsequently is decomposed with ice and water. The ether layer is decanted and is extracted with dilute hydrochloric acid; the resulting acid layer is made alkaline with concentrated ammonium hydroxide and is extracted with ether. On evaporation of the resulting ether solution, previously dried, there are obtained 50 grammes of an oil which is purified by fractional distillation. The fraction which distils between 150°–170° C/0.02 mm Hg (18 g), produces a white solid on treatment with hydrochloric acid-ether. Recrystallisation from acetone provides 13.5 g of the hydrochloride (m.p. = 221°–3° C). Total yield of recrystalized product = 22.5%.

Analysis: $C_{18}H_{28}NO_3Cl$. Calculated: $C = 63.24$, $H = 8.25$, $N = 4.09$, $Cl = 10.37$. Found: $C = 63.18$, $H = 8.45$, $N = 4.26$, $Cl = 10.12$.

PROPERTIES OF THE PRODUCTS OF THE INVENTION

Products
 I. — 1,3,4-trimethyl-2-(3,4,5-trimethoxybenzyl)-1,2,5,6-tetrahydropyridine;
 II. — 1,3,4-trimethyl-1-(3,4,5-trimethoxybenzyl)-1,2,5,6-tetrahydropyridinium chloride They are products with analgesic activity. The comparison analgesic used was dextropropoxyphene.

A. ACUTE TOXICITY

Acute toxicity studies were conducted in I.C.R. Swiss mice weighing $30 \pm 2$ g, of both sexes. The products were administered intraperitoneally (i.p.). The acute toxicity calculations were made by the method of Litchfield and Wilcoxon.

TABLE A

| Products | $LD_{50}$ | |
|---|---|---|
| I | 154.5 | mg/kg |
| II | 77 | mg/kg |
| Dextropropoxyphene | 140 | mg/kg |

B. ANALGESIC ACTIVITY

The analgesic activity was investigated in albino I.C.R. Swiss mice, using the acetic acid-induced writhing technique. Groups each of 10 mice were assembled.

The analgesics were injected intraperitoneally, and after 30 minutes 0.25 ml of a 1% solution of acetic acid was injected intraperitoneally. A control group received only acetic acid. The numbers of writhes made by each mouse was counted in the 20 minutes following administration of the acetic acid.

TABLE B

| Treatment | Dose | No. of writhes (x ± M.S.E.)[1] | P |
|---|---|---|---|
| I | 20 mg/kg | 74.5 ± 4.84 | p <0.001 |
| II | 20 mg/kg | 53.6 ± 4.7 | p <0.001 |
| Dextropropoxyphene | 25 mg/kg | 22.8 ± 4.74 | p <0.001 |
| Control | — | 112.2 ± 4.2 | — |

[1]Average value ± mean standard error

As may be seen from Table B, products I and II have analgesic activity.

Below there are examples of pharmaceutical compositions containing the following products as active ingredients.

I. 1,3,4-trimethyl-2-(3,4,5-trimethoxybenzyl)-1,2,5,6-tetrahydropyridine and its hydrochloride.

II. 1,3,4-trimethyl-1-(3,4,5-trimethoxybenzyl)-1,2,5,6-tetrahydropyridinium chloride.

The daily oral dose of product I is 2.23 mg per kg weight. A person weighing 70 kg would be given 150 mg per day, distributed over three doses of 50 mg.

The daily injectable dose of product I is 1.5 mg per kg. weight. A person weighing 70 kg would be given 105 mg per day, distributed over three doses of 35 mg each.

The daily oral dose of product II is similar to that of product I, i.e. 150 mg per day distributed over three doses of 50 mg.

EXAMPLE 1

| Hard gelatine capsules. Composition per capsule: | |
|---|---|
| 1,3,4-trimethyl-2-(3,4,5-trimethoxybenzyl)-1,2,5,6-tetrahydropyridine or its hydrochloride | 50 mg |
| Lactose | 100 mg |
| Magnesium stearate | 2.5 mg |

EXAMPLE 2

| Injectable solution. Composition per ampoule: | |
|---|---|
| 1,3,4-trimethyl-2-(3,4,5-trimethoxybenzyl)-1,2,5,6-tetrahydropyridine hydrochloride | 35 mg |
| Sodium chloride | 27 mg |
| Sodium metabisulphite | 3 mg |
| water for injectables q.s.p. | 3 ml. |

EXAMPLE 3

| Hard Gelatine Capsules. Composition per capsule: | |
|---|---|
| 1,3,4-trimethyl-1-(3,4,5-trimethoxybenzyl)-1,2,5,6-tetrahydropyridinium chloride | 50 mg |
| Lactose | 100 mg |
| Magnesium stearate | 2.5 mg |

We claim:

1. The compound selected from the group consisting of 1,3,4-trimethyl-2-(3,4,5-trimethoxybenzyl)-1,2,5,6-tetrahydropyridine and pharmaceutically acceptable acid addition salts thereof.

2. A composition exhibiting analgesic properties which comprises an analogesically effective amount of a compound selected from the group consisting of 1,3,4-trimethyl-2-(3,4,5-trimethoxybenzyl)-1,2,5,6-tetrahydropyridine and pharmaceutically acceptable acid addition salts thereof and a pharmaceutically acceptable carrier therefor.

3. A process for treating an animal comprising administering to the animal an analgesically effective amount of a compound selected from the group consisting of 1,3,4-trimethyl-2-(3,4,5-trimethoxybenzyl)-1,2,5,6-tetrahydropyridine and pharmaceutically acceptable acid addition salts thereof.

* * * * *